United States Patent
Santangelo et al.

(10) Patent No.: US 10,448,942 B2
(45) Date of Patent: Oct. 22, 2019

(54) FLEXIBLE DEFORMABLE SUTURE ANCHOR

(71) Applicant: Smith & Nephew, Inc., Memphis, TN (US)

(72) Inventors: Stephen Santangelo, Sturbridge, MA (US); Jeffrey Wyman, Naples, FL (US); Matthew E. Koski, Westford, MA (US)

(73) Assignee: Smith & Nephew, Inc., Memphis, TN (US)

(*) Notice: Subject to any disclaimer, the term of this patent is extended or adjusted under 35 U.S.C. 154(b) by 463 days.

(21) Appl. No.: 14/190,274

(22) Filed: Feb. 26, 2014

(65) Prior Publication Data

US 2014/0243893 A1 Aug. 28, 2014

Related U.S. Application Data

(60) Provisional application No. 61/769,400, filed on Feb. 26, 2013, provisional application No. 61/861,530, filed on Aug. 2, 2013.

(51) Int. Cl.
*A61B 17/04* (2006.01)
*A61F 2/08* (2006.01)

(52) U.S. Cl.
CPC .. *A61B 17/0401* (2013.01); *A61B 2017/0404* (2013.01); *A61B 2017/0406* (2013.01); *A61B 2017/0459* (2013.01); *A61F 2/0811* (2013.01); *A61F 2002/0864* (2013.01); *A61F 2002/0876* (2013.01); *A61F 2002/0882* (2013.01); *A61F 2002/0894* (2013.01)

(58) Field of Classification Search
CPC ............ A61B 17/0401; A61B 17/0487; A61B 2017/042; A61B 2017/0404; A61B 2017/0406; A61B 2017/0446; A61B 2017/0459; A61B 2017/0464; A61B 17/06166; A61B 2017/0618–06185; A61F 2/0811; A61F 2002/0817–0888
USPC .................................. 606/228–232
See application file for complete search history.

(56) References Cited

U.S. PATENT DOCUMENTS

| | | | |
|---|---|---|---|
| 6,660,008 B1 | 12/2003 | Foerster | |
| RE43,143 E * | 1/2012 | Hayhurst | ........... A61B 17/0401 606/232 |
| 8,303,604 B2 * | 11/2012 | Stone | ................. A61B 17/0401 606/139 |

(Continued)

FOREIGN PATENT DOCUMENTS

WO 2012151592 A2 11/2012

OTHER PUBLICATIONS

International Search Report, PCT/US2014/018512.
Office Action from related EPO Application No. 14709150.8-1664 dated Mar. 24, 2017.

*Primary Examiner* — Jonathan A Hollm
(74) *Attorney, Agent, or Firm* — Burns & Levinson, LLP; Joseph M. Maraia

(57) ABSTRACT

A deformable or flexible suture anchor having apertures secures a suture to a skeletal structure via holes drilled through the skeletal structure, and passing the suture therethrough. A deformable structure permits the anchor to resiliently deform or bend for passing through an aperture, and resume a size larger than the passed aperture for securement on an opposed side of the aperture.

9 Claims, 6 Drawing Sheets

(56) References Cited

U.S. PATENT DOCUMENTS

| | | | |
|---|---|---|---|
| 8,795,334 B2* | 8/2014 | Astorino | A61B 17/0057 606/232 |
| 2002/0029066 A1* | 3/2002 | Foerster | A61B 17/0469 606/228 |
| 2005/0137624 A1* | 6/2005 | Fallman | A61B 17/0057 606/213 |
| 2007/0185532 A1* | 8/2007 | Stone | A61B 17/0401 606/232 |
| 2009/0259251 A1* | 10/2009 | Cohen | A61B 17/06166 606/228 |
| 2009/0318961 A1 | 12/2009 | Stone | |
| 2010/0268273 A1* | 10/2010 | Albertorio | A61B 17/0401 606/232 |
| 2011/0098727 A1* | 4/2011 | Kaiser | A61B 17/0401 606/144 |
| 2011/0264141 A1* | 10/2011 | Denham | A61B 17/0401 606/232 |
| 2012/0059417 A1* | 3/2012 | Norton | A61B 17/0401 606/232 |
| 2012/0150203 A1* | 6/2012 | Brady | A61B 17/0401 606/148 |
| 2012/0290004 A1* | 11/2012 | Lombardo | A61B 17/0401 606/232 |
| 2013/0110165 A1* | 5/2013 | Burkhart | A61B 17/0401 606/232 |

* cited by examiner

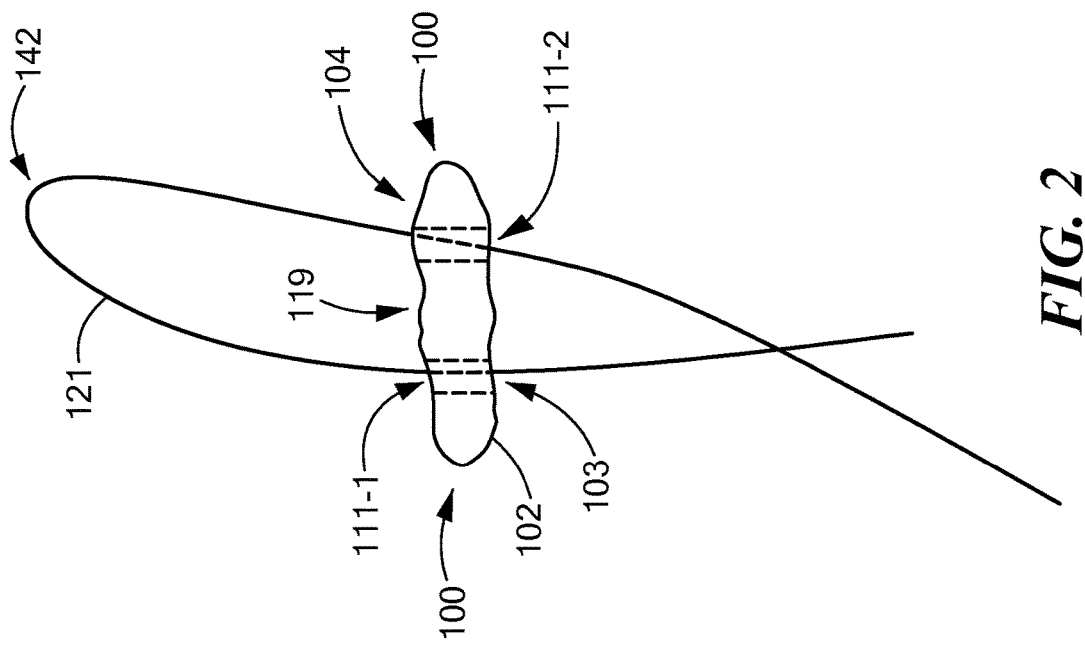
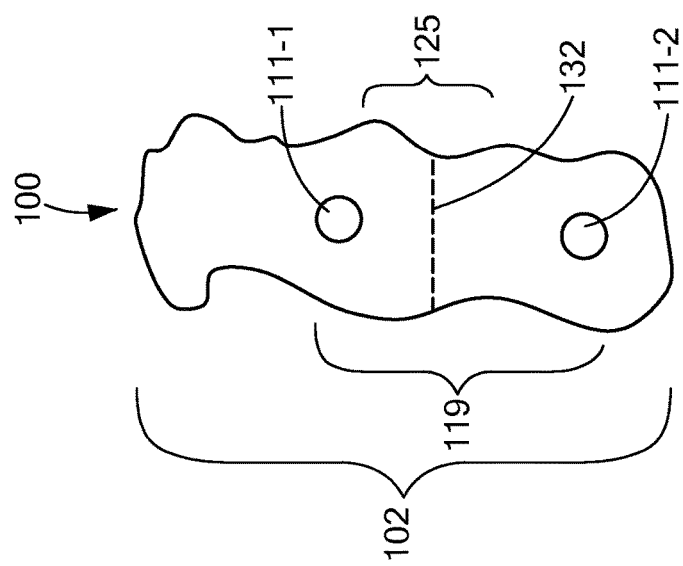

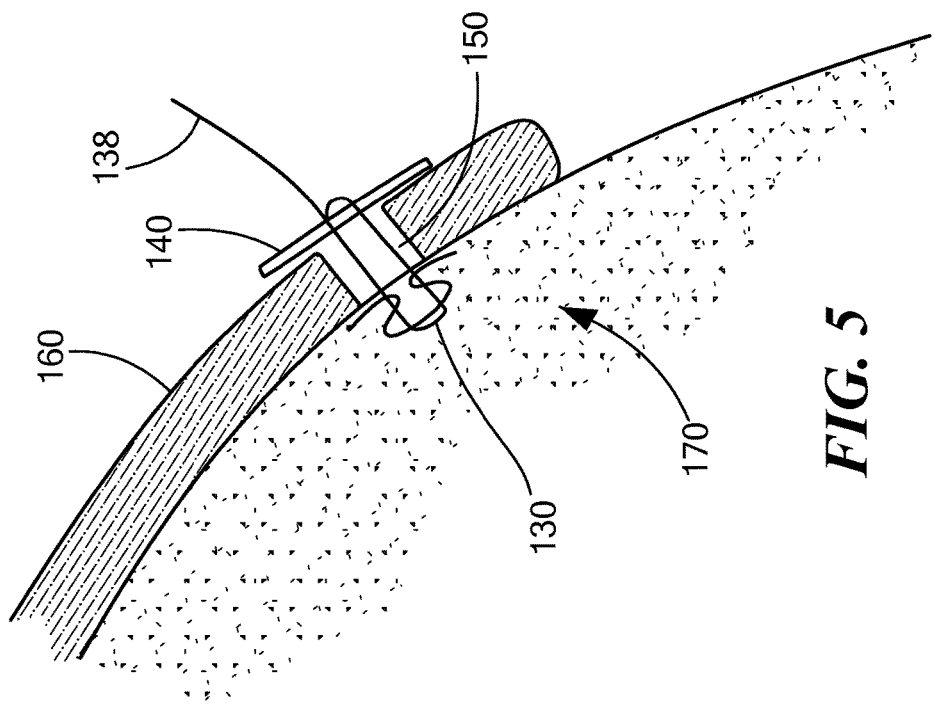
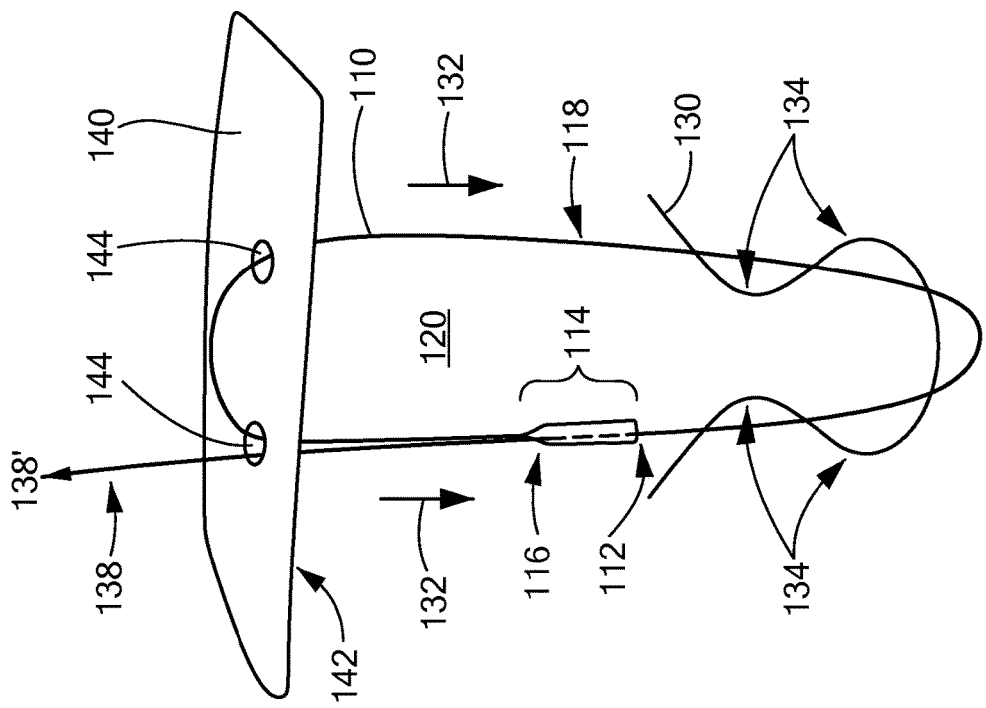

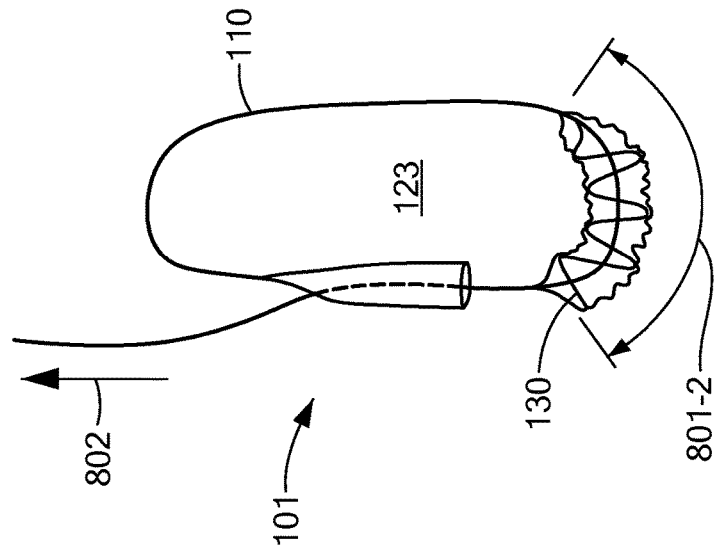
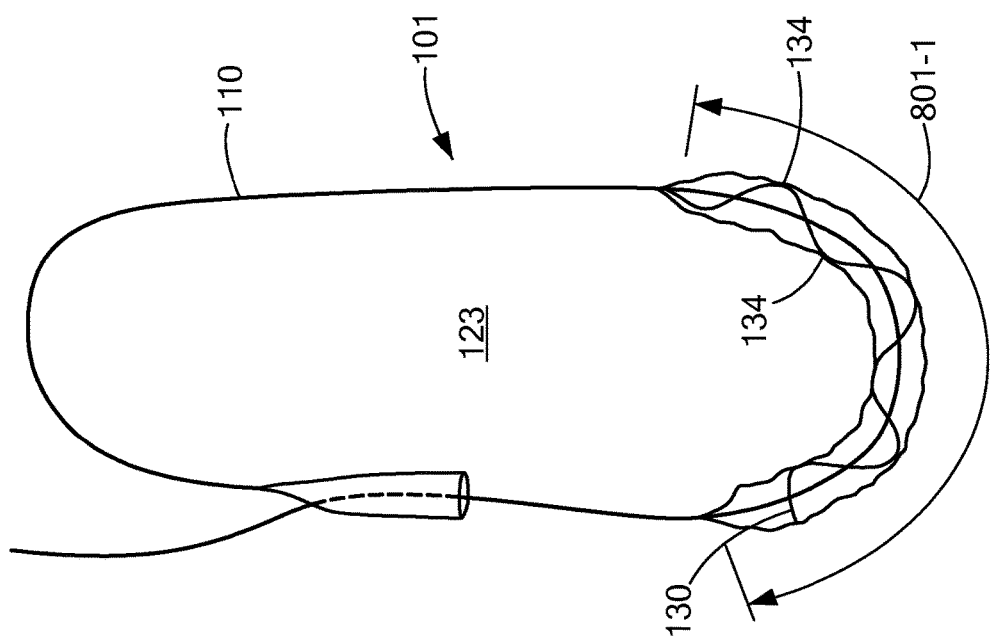

FLEXIBLE DEFORMABLE SUTURE ANCHOR

RELATED APPLICATIONS

This patent application claims the benefit under 35 U.S.C. § 119(e) of U.S. Provisional Patent Application Nos. 61/769,400, filed Feb. 26, 2013, entitled "SUTURE BASED HEADED TACK," and 61/861,530, filed Aug. 2, 2013, entitled "KNOTLESS SUTURE ANCHOR," both incorporated herein by reference in entirety.

BACKGROUND

Endoscopic surgical techniques frequently involve physical attachment to human skeletal joint structures. Sutures are often employed for securing reconstructive appliances to the skeletal structures. Sutures may also be employed to replace or supplement flexible connective tissue, such as tendons and ligaments. It is therefore desirable to securely attach the sutures to the skeletal structures such that the sutured attachment can withstand movement of the skeletal structures. Attachment mechanisms may vary based on the rigidity of the skeletal structure, since a hard bone surface withstands more force than a softer connective tissue, which is more prone to tearing or pulling through a suture attachment.

SUMMARY

Reconstructive surgery often employs surgical attachment techniques using a suture secured to a rigid skeletal member such as a bone or cartilage structure. Often soft tissue structures are adjacent and may need to be drilled, evacuated or otherwise accommodated. A deformable or flexible suture anchor having a plurality of apertures secures a suture to a skeletal structure via holes drilled through the skeletal structure, and passing the suture therethrough. A deformable structure permits the anchor to resiliently deform or bend for passing through an aperture, and resume a size larger than the passed aperture for securement on an opposed side of the aperture.

In a particular configuration, the suture anchor has a crossmember between the plurality of apertures (typically two) such that a continuous suture passes through both apertures and around the crossmember forming a loop, and through the holes in the skeletal structure. The suture anchor may be disposed through the skeletal hole with an insertion device for inserting the anchor along a smaller dimension (i.e. along its width) for transverse orientation following insertion. Since the transverse or rotated suture anchor is larger than the holes in the skeletal structure (i.e. bone), the suture anchor is drawn and engaged to the skeletal structure when the suture is contracted or pulled through the hole(s). The suture anchor binds the suture to the bone as the loop is pulled tight around the crossmember and forms a "T" with the suture as the length of the anchor is drawn against the surface of the skeletal member and perpendicular to the suture. The contoured anchor shape of the proposed approach facilitates mating with a skeletal structure and reinforcing areas of greatest strain, i.e. having a wider structure around the suture holes. Distal ends of the suture passed through the holes are then secured by any suitable means to maintain the suture taut and the suture anchor engaged by the suture looped around the crossmember.

In other contexts, it would be beneficial to provide a surgical anchor that can be inserted with a single insertion motion from a corresponding appliance, and which employs a knotless design cinchable by tension on a single suture strand. Unfortunately, conventional approaches suffer from the shortcoming that suture anchors are either all suture (anchor constructed itself of suture material) or knotless, but not both. The disclosed approach merges these approaches to define an all suture knotless anchor, capable of being delivered trans tissue. Features of the disclosed approach include the following: knotless design, radio lucent, all suture material construction, and provides a low profile suture pledget having a larger contact area under the pledget compared to standard anchors.

In another configuration, a knotless suture anchor as disclosed herein includes a cannulated suture forming a loop, in which the cannulated suture has a tubular wall defining an opening at an end of the suture, and the opening provides communication with a cannulated interior. The loop is defined by segment of the suture passed through the opening and into the cannulated interior a short distance and then passed out through a void in the tubular wall. A woven or mesh construction of the tubular wall permits passage to complete the looping in a so-called "finger trap" manner. The suture anchor is integrated with the cannulated suture, via a woven or mesh integration, such that the suture anchor is adapted for fixation at a surgical site. The pledget takes the form of a fixation member having an engagement surface, such as a substantially flat or planer surface facing the suture anchor and a plurality of apertures through which the suture loop passes, in which the loop engaging the apertures for drawing the engagement surface toward the suture anchor via tightening of the loop. Depending on the construction of the suture anchor, the engagement surface may be irregular or resilient, as in the case of a suture material anchor. In this manner, the surgical attachment is provided for tissue disposed between the engagement surface and the anchor.

In another configuration, a method of surgical attachment includes disposing a suture anchor through a surgical aperture, such that the suture anchor is compressibly deformable for permitting passage through the surgical aperture, and securing the suture anchor against the surgical aperture by restraining the suture anchor against the surgical aperture. The suture anchor deformability prevents subsequent passage through the surgical aperture. The suture anchor may be secured by drawing a suture strand through the surgical aperture and tightly against surgical tissue. Alternatively, securing may involve passing a distal end of a cannulated suture through a plurality of apertures in a fixation member, in which the fixation member has an engagement surface, and the cannulated suture has a tubular wall defining an opening at distal and proximate ends of the suture and an interior void defined by the cannulated interior. The method includes integrating a suture anchor into the tubular wall of the suture, the suture anchor adapted for fixation at a surgical site, and forming a loop in the cannulated suture, the opening providing communication with a cannulated interior, the loop defined by passing the suture passed through the opening into the cannulated interior and passed through a void in the tubular wall. A surgeon passes the distal end of the suture through at least one of the apertures in the fixation member and adjacent to the loop, and draws the engagement surface toward the suture anchor via tightening of the loop, the surgical attachment provided for tissue disposed between the engagement surface and the anchor.

The above configurations of deformable anchors may be employed individually or together, for example combining the knotless anchor with the deformable anchor as the pledget. Alternatively, the knotless anchor may be employed with a more rigid structure, also referred to as an ENDOBUTTON®, marketed commercially by Smith and Nephew, of Memphis, Tenn.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

FIG. 1 shows a top view of the deformable suture anchor;

FIG. 2 shows a side view of the suture anchor of claim 1 engaged by a suture;

FIG. 4 shows a side view of the knotless suture anchor assembly as disclosed herein;

FIG. 5 shows a cutaway view of a knotless suture and anchor assembly following surgical insertion.

FIG. 8A-8B show respective undeformed and deformed (compressed) configurations of FIGS. 4-6.

DETAILED DESCRIPTION

Figure 3A:
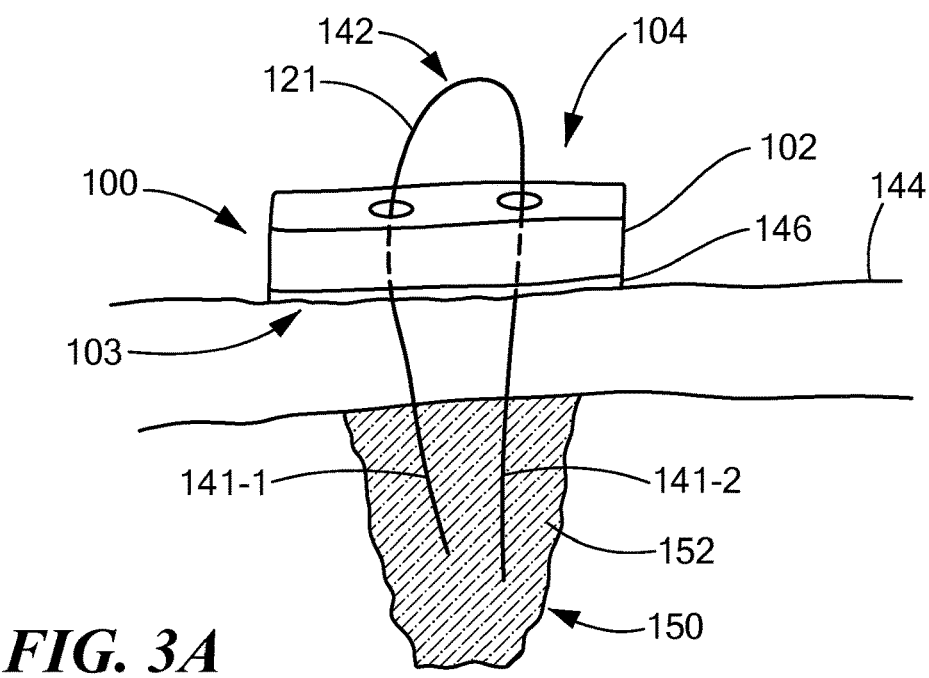
FIG. 3A shows the deformable suture anchor deployed in a recess.

Depicted below are various configurations of the proposed approach. The deformable anchor may be of any suitable deformable and/or resilient material, such as textile, plastic or rubber. FIG. 1 shows a top view of the deformable suture anchor 100.

The suture anchor body 102 has a plurality of apertures 111-1, 111-2 (111 generally) suitable for suture passage. The suture anchor therefore includes a body 102 having a plurality of apertures 111-1, 111-2 extending therethrough, such that the apertures are adapted for passing suture. The body 102 includes at least one crossmember 119, defined by the region between the apertures 111, such that the crossmember 119 is adapted for engagement with a suture loop 142 from a suture passed through at least two of the apertures 111, discussed further below with respect to FIG. 2. The body 102 may have an irregular and/or non-linear edges, due to construction of a resilient material such as textile, suture, or other flexible and/or deformable material, discussed further below.

The body 102 includes a flexible portion 125, adapted to deform along dotted line 132, for deforming the anchor 100 for insertion in a skeletal aperture, such that the flexible portion 125 is configured to return to an undeformed shape subsequent to insertion, in which the undeformed shape is unsuitable for passage through the skeletal aperture through which the deformed anchor 100 was passed. The flexible portion 125 may be part of the crossmember 119, and the body 102 may have a cutaway or more flexible portion at the dotted line 132 for facilitating a fold or other deformation in the anchor 100. Alternatively, the body 102 may be passed substantially undeformed in a lengthwise manner such that upon emerging, rotates 90 degrees for engaging a longitudinal side against the skeletal aperture. The undeformed anchor 100 is shown elongated and the deformed anchor folds substantially at a midsection defined by the dotted line 132. Once deployed, the anchor unfolds or undeforms, discussed below in FIG. 3.

FIG. 2 shows a side view of the suture anchor 100 of claim 1 engaged by a suture 121. The suture 121 passes through and emerges back to a common side 103 of the suture 121, thus defining a suture loop 142 on an opposed side 104. The suture loop 142 engages the crossmember 119 between the apertures 111-1, 111-2 for securing the suture on the opposed side 104. The suture 121 is knotted, secured in an anchor, or fixed by other suitable means from the common side 103.

FIG. 3A shows the deformable suture anchor deployed in a recess 150, such as a drilled hole. Referring to FIGS. 1-3B, in a particular arrangement, the body 102 is pulled against a surgical surface 144 or bone such that compression builds in the suture 121 due to the resilient nature of the body 102. A further resilient layer 146 may be provided between the body 102 and the surgical surface 144 for providing optimal compression forces and/or dispersion against the surgical surface 144. Suture ends 141-1, 141-2 (141 generally) are secured in a conventional anchor 152 for maintaining the compression force through tension in the suture 121. The deformable anchor 100 may be of any suitable deformable and/or resilient material, such as textile, plastic or rubber. The anchor 150 is disposed in a sufficiently firm material (i.e. bone) so as to adequately resist the tension from the suture 121. The surgical surface 144 may be a similar or less rigid surface such as tendons, ligaments or other connective or soft tissue.

Figure 3B:
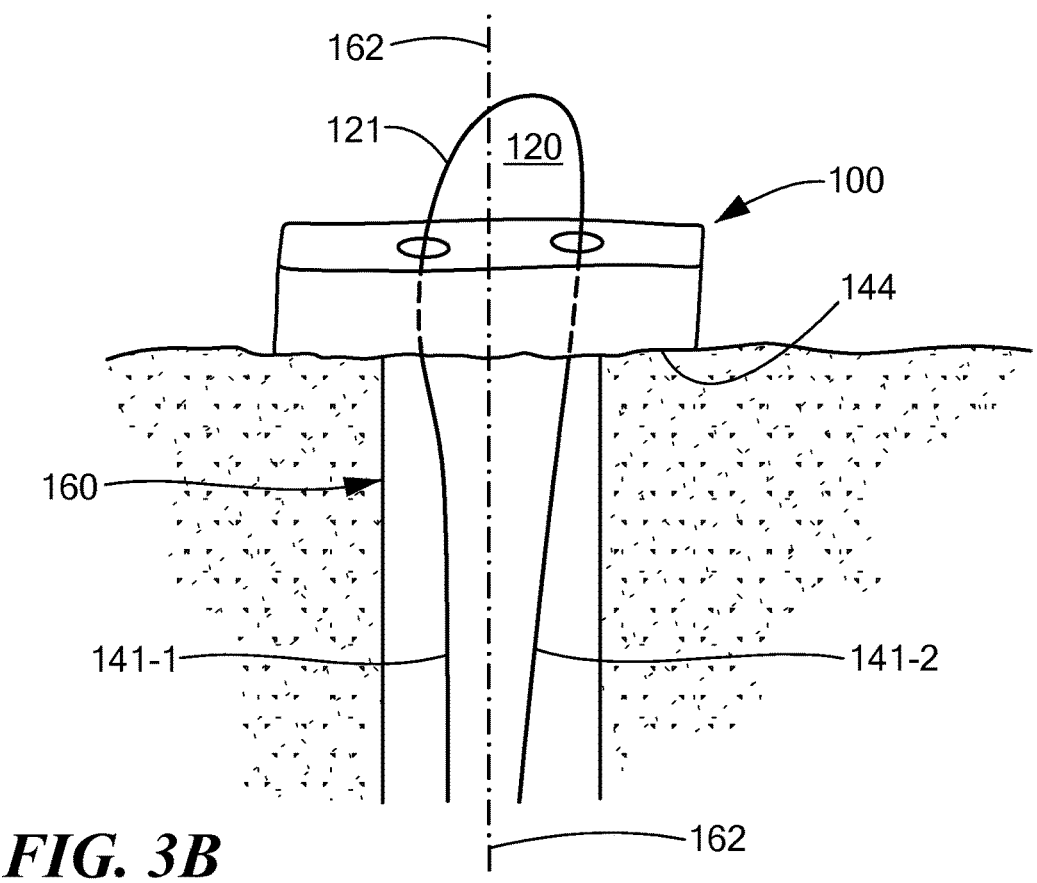
FIG. 3B shows the deformable suture anchor deployed through a bone tunnel.

FIG. 3B shows the deformable suture anchor deployed through a surgical aperture such as a bone tunnel 160. Following deformation for passage through a drilled hole or attachment to a recess, the body 102 returns to the undeformed shape disposing the elongated side of the anchor normal (lengthwise) to an axis 162 of the surgical aperture. The deformed body 102 is passed through the bone tunnel 160 by any suitable means, and undeforms (returns to undeformed state) upon emerging on the surgical surface 144. The suture 121 remains fixed by engagement with the crossmember 120 and the tension on the suture ends 141-1, 141-2, which are secured by any suitable means, such as knotting or anchoring, at a distal end of the bone tunnel away from the anchor 100. The undeformed anchor 100 thus has a length greater than a diameter of the surgical aperture defined by the bone tunnel 160, and therefore remains fixed, forming a "T" engagement with the suture 121 against the surgical surface 144.

Depicted below are various configurations of an alternate configuration of the proposed approach for a non-rigid knotless suture anchor. FIG. 4 shows a side view of a knotless suture and anchor assembly 101 as disclosed herein. The knotless suture anchor assembly 101 includes a cannulated suture 110 forming a loop 120, such that the cannulated suture 110 has a tubular wall defining an opening 112 at an end of the cannulated suture 110, in which the opening 112 provides communication with a cannulated interior, and the loop 120 is defined by a segment 114 of the suture passed through the opening 112 into the cannulated interior and passed through a void 116 in the tubular wall in a finger trap arrangement, similar to a noose construction. It should be noted that there is no knot, but like a noose, the suture 110 is allowed to slide thought the cannulation of section 114, such that the a distal end 138 passes through an opening 112 at the opposed (proximal) end, thus allowing the loop 120 diameter to be reduced.

A suture anchor 130 is integrated with the cannulated suture 110, via weaving or mesh construction to interleave, or "zig zag" around the suture 110 and is responsive to compress upon tightening of the loop 120, shown further in FIG. 3 below. The suture anchor 130 is adapted for fixation at a surgical site, and includes "all suture" construction, meaning that the suture anchor 130 itself is formed of resilient suture material.

A fixation member 140 takes the form of a pledget or Endobutton® having a planer engagement surface 142 and a plurality of apertures 144, such that the loop 120 engages the apertures 144 by passing the suture 110 therethrough for drawing the engagement surface 142 toward the suture anchor 130 via tightening of the loop 120, as shown by arrows 132, such that surgical attachment is provided for tissue disposed or compressed between the engagement surface 142 and the anchor 130. The fixation member 140 may be a deformable anchor 100 as in FIG. 1, or may exhibit a more rigid construction. The distal end 138 of the cannulated suture is passed between the interior void and an exterior region outside the cannulated suture 110 for passing through the apertures 144 to form a cinch end 138'.

FIG. 5 shows a cutaway view of a knotless suture and anchor assembly 101 following surgical insertion. Referring to FIGS. 4 and 5, in the configuration shown, the knotless suture anchor 101 is such that the tubular wall includes a tubular woven outer surface 118 around the cannulated interior defining an interior void. The suture anchor 130 is a non-rigid elongated member having alternate folds 134 and which is adapted to deform along the folds 134 for increasing a diameter of the elongated member for frictional engagement with a bone tunnel 150. In a particular configuration, the elongated member (suture anchor 130) is woven into the tubular wall of the suture 110, and is responsive to tightening of the cannulated suture 110 via the cinch end 138' for drawing the alternate folds 134 together. The suture anchor 130 may be an all suture anchor comprising suture material, such that the suture anchor 130 and the cannulated suture 110 are comprised of the same material. The suture anchor 130 may also be any suitable resilient or textile material.

The disclosed non-rigid knotless suture anchor assembly 101 is employed in a method of securing tissue 160 to other skeletal or connective members such as bone 162. The distal end 138 of a cannulated suture 110 is passed through the plurality of apertures 144 in the fixation member 140, such that the fixation member 140 has a planer surface 142, and the cannulated suture 110 has a tubular wall defining an opening at distal and proximate ends of the suture 110 and an interior void defined by the cannulated interior of the suture 110. The suture anchor 130 is integrated into the tubular wall 118 of the suture, such that the suture anchor 130 is adapted for fixation at a surgical site 170. The distal end 138 forms a loop 120 in the cannulated suture 110, via the opening 112 that provides communication with the cannulated interior, in which the loop 120 is defined by passing the suture 110 through the opening 112 into the cannulated interior and passed through a void 116 in the tubular wall 118. The distal end 138 of the suture is passed through at least one of the apertures 144 in the fixation member 140 and adjacent to the suture 110 passing through the same aperture 144. Insertion of the surgical anchor 130 causes it to compress via the alternate folds 134 upon pulling on the distal end 138 acting as a cinch for drawing the engagement surface 142 toward the suture anchor 130 via tightening of the loop 120, such that surgical attachment is provided for the tissue 160 disposed between the engagement surface 142 and the bone 162.

Figure 6:
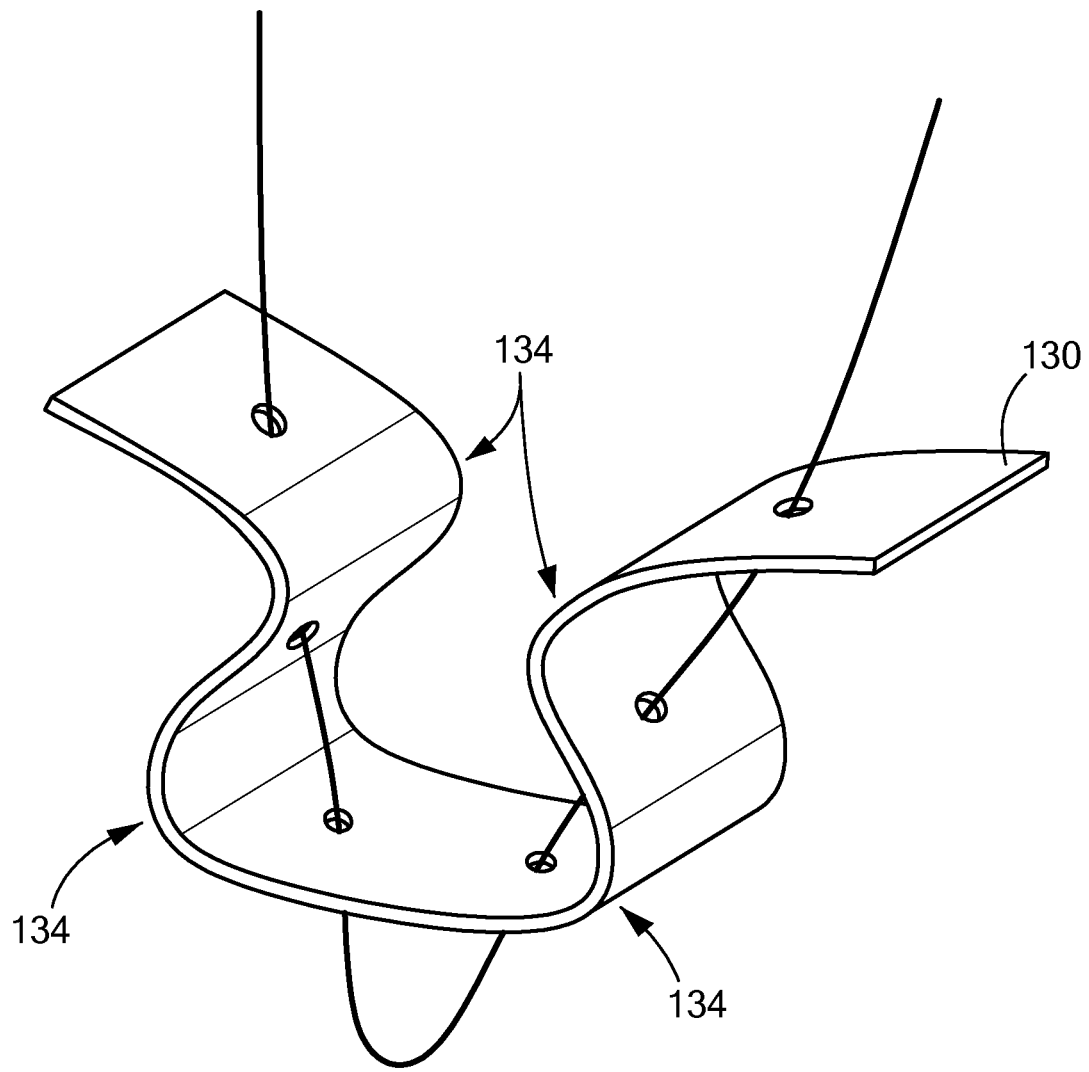
FIG. 6 shows the integration of the cannulated suture and the suture anchor.

FIG. 6 shows the integration of the cannulated suture and the suture anchor. Referring to FIGS. 4-6, the suture anchor 130 may engage the cannulated suture in a variety of ways for expanding the suture anchor 130 upon tightening of the loop 120 via the distal end 138. In the example of FIG. 3, the cannulated suture 110 passes through apertures 131 in the suture anchor 130. Upon tightening of the loop 120, drawing the cannulated suture 110 closed, the suture anchor 130 is drawn along the folds 134 for expanding in a bone tunnel 150 or other installation void.

In the configurations above, a deformable section (shown by the flexible section 125 and the folds 134 in the suture anchor 130) effectively provides a suture anchor with varying dimensions of length and width such that they may be passed through a suture aperture such as a bone tunnel for insertion, and achieve an alternate dimension for fixation. Depending on the "undeformed" or "at rest" state of the deformable suture anchor, the state of deformation may provide for insertion or fixation. Generally, the insertion state is a temporary compression or expansion which allows passage through an aperture, followed by fixation which causes the suture anchor to achieve a dimension preventing passage through the aperture. In colloquial terms, the suture anchor may be "squeezed" or "squished" through a hole, or inserted through and then "squished" or "squeezed" to enlarge the anchor against passage.

Figure 7A:
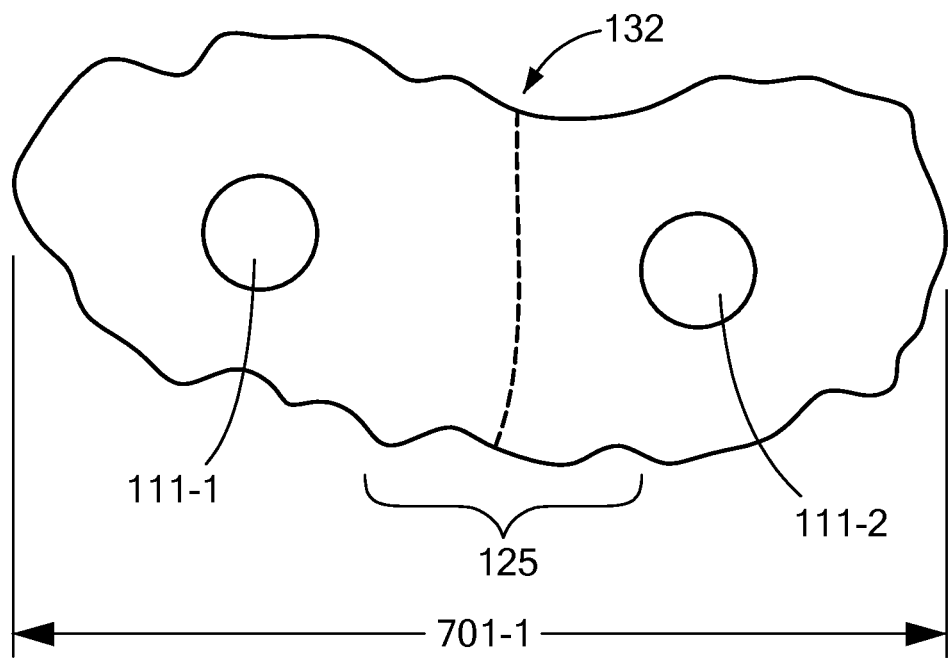
FIGS. 7A and 7B show respective undeformed and deformed (compressed) suture anchors of the configuration of FIG. 1-3B.
Figure 7B:
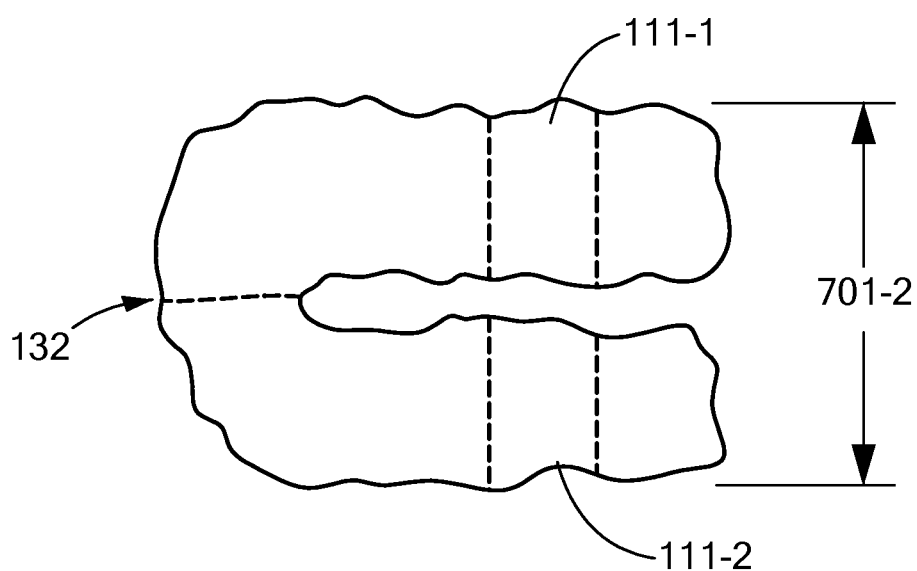

FIGS. 7A and 7B show respective undeformed and deformed (compressed) suture anchors of the configuration of FIG. 1-3B. Referring to FIGS. 1-3, 7A and 7B, the body 102 of the suture anchor 101 defines a first dimension 701-1 in an unfolded, or uncompressed state. In FIG. 7B, the anchor 101 is folded along the deformable section 125 at the fold line 132. The folded anchor has a second dimension 701-2, which allows the anchor 101 to pass through a bone tunnel 150 or other surgical aperture. Following insertion, the anchor 101 is allowed to resume an undeformed state 701-1, which prevents passage back though the aperture due to a "T" formation with the suture 121.

The suture anchor of FIGS. 7A and 7B therefore includes a deformable section 125, the deformable section 125 varying a dimension 701-1, 701-2 of the suture anchor 101 for restraining the suture anchor 101 against a surgical aperture such as a bone tunnel 160. The surgical anchor 101 includes at least one aperture 111, or suture passage (2 shown), such that the suture passage 111 permits passage of the 121 suture through the anchor and into the surgical aperture. The suture anchor 100 has a first dimension allowing passage through the surgical aperture, and a second dimension restricting passage through the surgical aperture, the first 701-1 and second 701-2 dimensions based on the deformable section 125 (either the first or second dimension may be the smaller of the two for permitting passage).

The deformable section 125 is responsive to external forces for modifying a cross section width, such as from an insertion tool or pulling on the suture 121 via the crossmember 120, in which the deformation permits passage through the surgical aperture and subsequent expansion for preventing passage through the surgical aperture. In the example of FIGS. 1-3, 7A and 7B, the deformable section 125 defines a fold 132 along a length or width of the suture anchor, such that the deformable suture anchor 101 is adapted for passage through the surgical aperture when folded as in FIG. 7B. The deformable section 125 is therefore adapted to unfold following passage through the surgical aperture, such that the unfolded deformable section 125 defines an elongated suture anchor 100 having body 102 for restraining the suture anchor against the surgical aperture.

The suture anchor 100 therefore includes at least one crossmember 120 between the surgical apertures 110, such that the crossmember is adapted for engagement with a suture loop 142 from a suture 121 passed through at least two of the apertures 100. The undeformed anchor 100, having body 102, is elongated and the deformed anchor folds substantially at a midsection or fold 132 (FIG. 7B), and returns to an undeformed shape (FIG. 7A) disposing the elongated side of the anchor normal to an axis of the skeletal aperture or bone tunnel 160.

FIGS. 8A-8B show respective undeformed and deformed (compressed) configurations of FIGS. 4-6. Referring to FIGS. 4-6, 8A and 8B, a knotless anchor 101 is shown that forms a suture loop 123 by passing the suture back through a mesh-constructed cannulated interior of itself and back out through a gap or aperture in the mesh. An elongated anchor structure 130 alternates folds 134 around the suture loop 123, such that the suture 118 passes through holes 131 or apertures in the anchor 130, which may also be a mesh construction. Upon tightening of the loop 123, the folds 134 are pulled together, causing the anchor to contract from a first dimension (length) 801-1 to a second dimension 801-2, and at the same time expand in width as the suture loop is closed, or tightened by drawing the suture 110 in the direction of arrow 802. The mesh section 114 may also expand, contributing to the holding force of the deformed, or compressed anchor 130.

In the examples shown, the knotless suture anchor 101 is a non-rigid elongated member having alternate folds 134 and adapted to deform along the folds 134 for increasing a diameter of the elongated member (such as anchor 130) for frictional engagement with a bone tunnel 160, securing the suture loop and thereby preventing passage of the suture via pulling through the bone tunnel 160. In the example shown, the deformable section may be a mesh section defining a portion of the cannulated suture, such that passing through the gap in the cannulated suture forms the loop 123 responsive to closing from tightening the cannulated suture (arrow 802) for closing the loop 123 and compressing the mesh for deforming the suture anchor 130, shown as compressed dimension 801-2. The suture anchor is adapted for engagement with a fixation member 140 having an engagement surface 142 and a plurality of apertures 144, in which the loop 123 engages the apertures for drawing the engagement surface 142 toward the suture anchor 130 via tightening 802 of the loop 123 and providing surgical attachment for tissue disposed between the engagement surface 142 and the suture anchor. The fixation member may be a resilient or textile fixation member 100 as disclosed above, or may be a rigid construction.

While the disclosed configurations have been described with reference to exemplary embodiments, it will be understood by those skilled in the art that various changes may be made and equivalents may be substituted for elements thereof without departing from the scope of the invention. Therefore, it is intended that the invention not be limited to the particular embodiments disclosed for carrying out this invention, but that various configurations will include all embodiments falling within the scope of the appended claims.

The invention claimed is:

1. A knotless suture anchor assembly comprising:
   a cannulated suture having a tubular wall defining a cannulated interior between a distal opening at a distal end of the cannulated suture and a proximate opening at a proximate end of the cannulated suture, the proximate opening providing communication with the cannulated interior, the distal end of the cannulated suture passing through the proximate opening to form a loop before passing through a void in the tubular wall;
   a suture anchor integrated with the cannulated suture, the suture anchor adapted for fixation at the surgical site, the suture anchor including a plurality of apertures including a first aperture, a second aperture, and a third aperture on a first end of the suture anchor and a fourth aperture, a fifth aperture, and a sixth aperture on a second end of the suture anchor, the suture anchor further including a plurality of deformable folds, the deformable folds deposed between the apertures and forming more deformable sections of the suture anchor across a width of the suture anchor; and
   a fixation member having an engagement surface and a plurality of apertures, the loop engaging the apertures for drawing the engagement surface toward the suture anchor via tightening of the loop, whereby the knotless suture anchor assembly is configured to provide surgical attachment for tissue disposed between the engagement surface and the anchor,
   wherein:
   the suture anchor includes a first surface facing the fixation member and a second surface opposite the first surface and facing away from the fixation member;
   the loop passes between: the first aperture and second aperture on the second side of the suture anchor; the second aperture and the third aperture on the first side of the suture anchor; the third aperture and the fourth aperture on the second side of the suture anchor; the fourth aperture and the fifth aperture on the first side of the suture anchor; and the fifth aperture and the sixth aperture on the second side of the suture anchor;
   the deformable folds include a first deformable fold between the first aperture and the second aperture, a second deformable fold between the second aperture and the third aperture, a third deformable fold between the fourth aperture and the fifth aperture, and a fourth deformable fold between the fifth aperture and the sixth aperture; and
   the proximate end of the cannulated suture is positioned between the suture anchor and the fixation member.

2. The knotless suture anchor assembly of claim 1 wherein the tubular wall includes a tubular woven outer surface around the cannulated interior defining an interior void.

3. The knotless suture anchor assembly of claim 2 wherein the suture anchor comprises textile suture material, and wherein the distal end of the cannulated suture is configured to pass between the interior void and an exterior region outside the cannulated suture.

4. The knotless suture anchor assembly of claim 1 wherein the suture anchor and the cannulated suture are comprised of the same material.

5. The knotless suture anchor assembly of claim 1 wherein the fixation member is substantially non-deformable in that the knotless suture anchor assembly is configured such that tension forces from the tightening of the loop change a first dimension of the suture anchor without substantially deforming the fixation member during use thereof to compress tissue between the engagement surface of the fixation member and the suture anchor.

6. The knotless suture anchor assembly of claim 1 wherein in an at rest state, the suture anchor has an enlarged surface and resists passage through a surgical aperture in a bone; and in an insertion state, the deformable section is temporarily compressed to a smaller dimension for insertion through the aperture, the deformable section returning to the at rest state within the bone in response to the tightening of the loop.

7. A method of securing tissue comprising:

passing a cannulated suture through a plurality of apertures in a fixation member, the fixation member having an engagement surface, the cannulated suture having a tubular wall defining a cannulated interior between a distal opening at a distal end of the cannulated suture and a proximate opening at a proximate end of the cannulated suture, the proximate opening providing communication with the cannulated interior;

integrating a suture anchor with the cannulated suture, the suture anchor having a first surface facing the fixation member and a second surface opposite the first surface and facing away from the fixation member, the suture anchor adapted for fixation at a surgical site, the suture anchor including a plurality of apertures including a first aperture, a second aperture, and a third aperture on a first end of the suture anchor and a fourth aperture, a fifth aperture, and a sixth aperture on a second end of the suture anchor, the suture anchor further including a plurality of deformable folds, the deformable folds deposed between the apertures and forming more deformable sections of the suture anchor across a width of the suture anchor, the deformable folds including a first deformable fold between the first aperture and the second aperture, a second deformable fold between the second aperture and the third aperture, a third deformable fold between the fourth aperture and the fifth aperture, and a fourth deformable fold between the fifth aperture and the sixth aperture;

forming a loop in the cannulated suture by passing the distal end of the cannulated suture:

through the first aperture on the first side of the suture anchor and through the second aperture on the second side of the suture anchor such that the loop passes between the first aperture and the second aperture on the second side of the suture anchor;

through the third aperture on the first side of the suture anchor such that the loop passes between the second aperture and the third aperture on the first side of the suture anchor;

through the fourth aperture on the second side of the suture anchor such that the loop passes between the third aperture and the fourth aperture on the second side of the suture anchor;

through the fifth aperture on the first side of the suture anchor such that the loop passes between the fourth aperture and the fifth aperture on the first side of the suture anchor; and through the sixth aperture on the second side of the suture anchor such that the loop passes between the fifth aperture and the sixth aperture on the second side of the suture anchor; and through the proximate opening into the cannulated interior and out through a void in the tubular wall;

after the loop has been formed, passing the distal end of the suture through at least one of the apertures in the fixation member and adjacent to the loop, the proximate end of the cannulated suture being positioned between the suture anchor and the fixation member; and drawing the engagement surface toward the suture anchor via tightening of the loop, whereby surgical attachment is provided for tissue disposed between the engagement surface and the suture anchor.

8. The method of claim 7 wherein the engagement surface is a substantially planar engagement surface, wherein the fixation member has sufficient rigidity to maintain a substantially planar shape of the substantially planar engagement surface before and after the drawing the engagement surface of the fixation member toward the suture anchor via tightening of the loop.

9. The method of claim 7 wherein the loop is formed by looping the cannulated suture through apertures in each of the suture anchor and the fixation member and slidably securing a proximate end of the suture relative to a distal end of the suture whereby the distal end of the cannulated suture is a single slidable free end of the loop, drawing the single slidable free end tightening the loop.

* * * * *